United States Patent [19]
Wolin et al.

[11] Patent Number: 6,133,291
[45] Date of Patent: *Oct. 17, 2000

[54] N-(IMIDAZOLYLALKYL)SUBSTITUTED CYCLIC AMINES AS HISTAMINE-H$_3$ AGONISTS OR ANTAGONISTS

[75] Inventors: Ronald Wolin, Bedminister; Stuart B. Rosenblum, West Orange; Adriano Afonso, West Caldwell, all of N.J.

[73] Assignee: Schering Corporation, Kenilworth, N.J.

[*] Notice: This patent issued on a continued prosecution application filed under 37 CFR 1.53(d), and is subject to the twenty year patent term provisions of 35 U.S.C. 154(a)(2).

[21] Appl. No.: 09/173,642

[22] Filed: Oct. 16, 1998

[51] Int. Cl.$^7$ .................. A61K 31/445; C07D 401/06
[52] U.S. Cl. .................. 514/326; 514/212; 514/397; 540/603; 546/210; 548/314.7
[58] Field of Search .................. 514/212, 326, 514/397; 540/603; 546/210; 548/314.7

[56] References Cited

U.S. PATENT DOCUMENTS

| | | | |
|---|---|---|---|
| 4,006,137 | 2/1977 | Haugwitz et al. | 514/326 |
| 4,238,493 | 12/1980 | Roantree et al. | 514/326 |
| 5,463,074 | 10/1995 | Shih et al. | 548/314.7 |
| 5,807,872 | 9/1998 | Shih et al. | 514/326 |

FOREIGN PATENT DOCUMENTS

| | | |
|---|---|---|
| 420396 A2 | 4/1991 | European Pat. Off. . |
| 62-87573 | 4/1987 | Japan . |
| 93/01812 A1 | 2/1993 | WIPO . |
| 93/12093 | 6/1993 | WIPO . |
| 94/19309 | 12/1994 | WIPO . |
| 95/14007 | 5/1995 | WIPO . |

OTHER PUBLICATIONS

Lee "Preparation of acylpyrrolomethylimidazoles and analogs as farnesyl transferase inhibitors" CA 131:31940, 1999.
Robin et al. "Design or potent nonthiurea H3 receptor histamine antagonists" J. Med. chem. v.38, pp. 3342–3350, 1995.
darling et al. "Synthesis of histamine analogs" CA 84:90076, 1976.
Howson, *Bioorg. & Med. Chem. Letters*, 2(1), 77–78 (1992).
Van der Groot, *Eur. J. Med. Chem.*, 27, 511–517 (1992).
Clapham, *J. Psychopharmacol.*, (Abstracts book), A17 (1993).
Clapham, *British J. Pharm. Suppl.*, 110, Abstract 65P (1993).
Yokoyama, *European J. Pharmacology*, 234, 129–133 (1993).
Schlicker, *British J. Pharmacology*, 112, 1043–1048 (1994).
Leurs, *Prog. Drug. Res.*, 39, 127–165 (1992).
Lipp, "The Histamine Receptor", ed. Schwartz and Haas, Wiley–Liss Publications, New York, New York, 57–72 (1992).
Bagley, *J. Med. Chem.*, 34, 827–841 (1991).
Hey, *European J. Pharmacology*, 294, 329 (1995).

*Primary Examiner*—Ceila Chang
*Attorney, Agent, or Firm*—Palaiyur S. Kalyanaraman

[57] ABSTRACT

The present invention discloses novel N(imidazolylalkyl)-substituted cyclic amine compounds which have excellent histamine-H$_3$ receptor antagonist activity as well as methods for preparing such compounds. In another embodiment, the invention discloses pharmaceutical compositions comprising such cyclic amines as well as methods of using them to treat allergy, inflammatory and CNS-related diseases.

27 Claims, No Drawings

N-(IMIDAZOLYLALKYL)SUBSTITUTED CYCLIC AMINES AS HISTAMINE-$H_3$ AGONISTS OR ANTAGONISTS

FIELD OF THE INVENTION

The present invention relates to N-(imidazolylalkyl) substituted cyclic amine compounds having valuable pharmacological properties, especially central nervous system ("CNS") activities and activity against inflammatory disease and allergic conditions. Compounds of this invention are agonists or antagonists of the histamine-$H_3$ receptor.

BACKGROUND OF THE INVENTION $H_3$ receptor sites are known and are of current interest to those skilled in the art as a therapeutic target. U.S. Pat. No. 4,767,778 (Arrange et al) discloses certain imidazoles that behave as agonists of the $H_3$ receptors in rat brain. European Patent Application No. 0 420 396 A2 (Smith Kline & French Laboratories Limited) and Howson et al., (*Bioorg. & Med. Cherm. Letters*, (1992), Vol. 2 No. 1, pp. 77–78) describe imidazole derivatives having an amidine group as H3 agonists. Van der Groot et al. (*Eur. J. Med. Chem.* (1992) Vol. 27, pp. 511–517) describe isothiourea analogs of histamine as potent agonists or antagonists of the histamine-H3 receptor, and these isothiourea analogs of histamine overlap in part with those of the two references cited above. Clapham et al. ["Ability of Histamine-$H_3$ Receptor Antagonists to Improve Cognition and to Increase Acetylcholine Release in vivo in the Rat", *British Assn. for Psychopharmacology*, Jul. 25–28 (1993), reported in *J. Psychopharmacol.* (Abstr. Book), A17] describe the ability of histamine-$H_3$ receptor antagonists; to improve cognition and to increase release of acetylcholine in vivo in the rat. Clapham et al. ["Ability of the selective Histamine-$H_3$ Receptor Antagonist Thioperamide to improve Short-term Memory and Reversal Learning in the Rat", *Brit. J. Pharm. Suppl.*, 1993, 110, Abstract 65P] present results showing that thioperamide can improve short-term memory and reversal learning in the rat and implicate the involvement of $H_3$ receptors in the modulation of cognitive function. Yokoyama et al. ["Effect of Thioperamide, a Histamine-$H_3$ Receptor Antagonist, on Electrically Induced Convulsions in Mice", *Eur. J. Pharmacol.*, (1993), Vol. 234, pp. 129–133] report how thioperamide decreased the duration of each phase of convulsion and raised the electroconvulsive threshold, and go on to suggest that these and other findings support the hypothesis that the central histaminergic system is involved in the inhibition of seizures. International Patent Publication No. WO 9301812-A1 (SmithKline Beecham PLC) describes the use of S-[3-(4(5)-imidazolyl)propyl] isothiourea as a histamine-$H_3$ antagonist, especially for treating cognitive disorders, e.g. Alzheimer's disease and age-related memory impairment. Schlicker et al. ["Novel Histamine-$H_3$ Receptor Antagonists: Affinities in an $H_3$ Receptor Binding Assay and Potencies in Two Functional $H_3$ Receptor Models", *British J. Pharmacol.*, (1994), Vol. 112, 1043–1048] describe a number of imidazolylalkyl compounds wherein the imidazolylalkyl group is bonded to a guanidine group, an ester group an amide group, a thioamide group and a urea group, and compared these to thioperamide. Leurs et al. ["The Histamine-$H_3$-receptor: A Target for Developing New Drugs", *Progr. Drug Res.* (1992), Vol. 39, pp. 127–165] and Lipp et al. ["Pharmacochemistry of $H_3$-receptors" in The Histamine Receptor, eds.: Schwartz and Haas, Wiley-Liss, New York (1992), pp. 57–72] review a variety of synthetic $H_3$ receptor antagonists, and Lipp et al. (ibid.) have proposed the necessary structural requirements for an $H_3$ receptor antagonist.

WO 35/14007 claims $H_3$ receptor antagonists of the formula

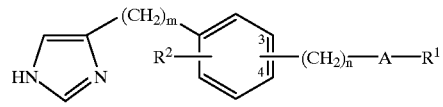

wherein A, m, n, $R^1$ and $R^2$ are defined therein. The compounds are disclosed as being useful for treating various disorders, in particular such caused by allergy-induced responses.

WO 93/12093 discloses imidazolylmethyl piperazines and diazepines as $H_3$ antagonists. U.S. patent application, Ser. No. 08/965,754, filed Nov. 7, 1997, discloses imidazolylalkyl substituted heterocyclic ring compounds as $H_3$ receptor antagonists. U.S. patent application, Ser. No. 08/966,344, filed Nov. 7, 1997, discloses phenylalkylimidazoles as $H_3$ receptor antagonists.

Reference is also made to U.S. Application, Ser. No. 08/689,951, filed Aug. 16, 1996 which claims the combined use of a histamine-$H_1$ receptor antagonist and a histamine-$H_3$ receptor antagonist for treatment of allergy-induced airway responses.

Reference is also made to J. R. Bagley et al, *Journal of Medicinal Chemistry*, (1991), Vol. 34, 827–841, which discloses, among others, N-(imidazolylalkyl) substituted cyclic amine compounds useful as analgesics such as the amine compound with the formula:

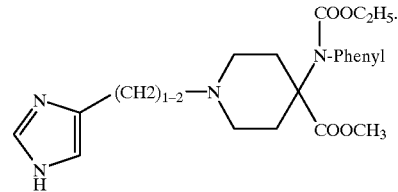

In view of the art's interest in compounds which affect the $H_3$ receptors, novel compounds having agonist or antagonist activity on $H_3$ receptors would be a welcome contribution to the art. This invention provides just such a contribution by providing novel compounds having $H_3$ agonist or antagonist activity.

SUMMARY OF THE INVENTION

In one embodiment, this invention provides novel imidazole compounds, having $H_3$ agonist or antagonist activity. The inventive compounds are N-(imidazolylalkyl)-substituted cyclic amines having the general Formula I:

Formula I

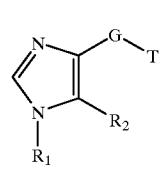

wherein $R_1$ is selected from the group consisting of H, —OCO—$R_7$, and —CO$_2R_7$, with $R_7$ being a substituted or unsubstituted alkyl or aryl, the substituents on said substituted alkyl or aryl being selected from the group consisting of hydrogen, alkyl, alkenyl, alkynyl, aryl, aralkyl, cycloalkyl, heterocyclic and halogen;

$R_2$ is selected from the group consisting of H, hydroxyl or halogen;

G is a spacer moiety selected from the group consisting of a $C_3$–$C_7$ straight chain alkyl, a $C_2$–$C_7$ alkene or a $C_2$–$C_7$ alkyne, with said straight chain alkyl, alkene or alkyne being optionally substituted with one or more $R_7$ groups; and T which represents a cyclic amine is a ring moiety selected from the group consisting of a, b, c or d below:

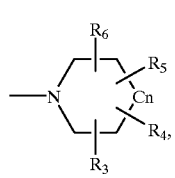

a

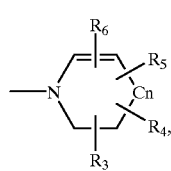

b

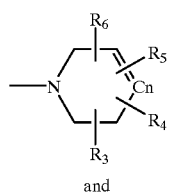

c and

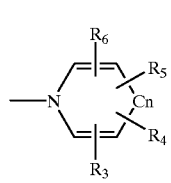

d wherein n is an integer from 0–3, and $R_3$, $R_4$, $R_5$ and $R_6$ can be the same or different with the proviso that any two of said $R_3$, $R_4$, $R_5$, and $R_6$ can be bound to the same or different carbon atom of ring T with a maximum valency of four at any carbon, with said $R_3$, $R_4$, $R_5$ and $R_6$ being independently selected from the group consisting of H, substituted or unsubstituted $C_1$–$C_6$ alkyl, substituted or unsubstituted $C_1$–$C_6$ alkenyl, substituted or unsubstituted $C_1$–$C_6$ alkynyl, aryl, aralkyl, alkylaryl, cycloalkyl, heterocyclic, —C—O—$R_8$, —C(=O)$R_8$, —CO$_2R_8$, —OC(O)$R_8$, —NH$_2$, —NHR$_8$, —N(R$_8$)$_2$, —NR$_8R_9$, —SR$_8$, —SO$_2R_8$, S(O)R$_8$, —OH, —OR$_8$, —CH$_2$OR$_8$, —CH$_2$NH$_2$, —CH$_2$N(R$_8$)$_2$, —CH$_2$NHR$_8$, —CH$_2$SR$_8$, —C(O)—NHR$_8$, —C(O)NR$_8R_9$, —CN, —NO$_2$, —NR$_8$—CO—, —C(NH)—NR$_8$, —C(=NR$_8$)NR$_9$, —NR$_8$—C(NH)—, —NHR$_8$(CO)NHR$_9$, —(O—CR$_8$—CR$_8$—O)—, —CX(R$_8$)$_2$, —CX$_2R_8$, —CX$_3$, —OCX$_3$, —N(R$_8$)—S(O)R$_9$, —N(R$_8$), —SO$_2R_9$, (=O), (=NH—OR$_8$), —C(=S)R$_8$, —NCR$_8$, —NOR$_8$, —NR$_8R_9$—SO$_2$—NR$_8R_9$, —OPO$_2R_8$, —P$^+$(R$_8$)$_3$ X$^-$, —SO$_3$H, fused heteroaryl, and (=CR$_8$) wherein $R_8$ and $R_9$ are independently H or $C_1$–$C_6$ alkyl, aryl, aralkyl, alkylaryl, cycloalkyl or heterocyclic, and X is a halogen.

Also included in the invention are tautomers, enantiomers and other optical isomers of compounds of Formula I, as well as pharmaceutically acceptable salts and solvates thereof.

A further feature of the invention is pharmaceutical compositions containing as active ingredient a compound of Formula I (or salt, solvate or isomers) together with a pharmaceutically acceptable carrier or excipient.

The invention also provides methods for preparing compounds of Formula I, as well as methods for treating diseases such as, for example, inflammation, allergy, diseases of the GI-tract, cardiovascular disease, or disturbances of the central nervous system. The latter methods comprise administering to a patient suffering from said disease or diseases a therapeutically effective amount of a compound of Formula I, or pharmaceutical compositions comprising a compound of Formula I.

The invention also includes the aspect of using the claimed cyclic amine compound in combination with a histamine-$H_1$ receptor antagonist for treatment of allergy-induced airway (e.g., upper airway) responses.

DETAILED DESCRIPTION OF THE INVENTION

In one embodiment, the present invention provides novel N-imidazolylalkyl substituted cyclic amine compounds of Formula I:

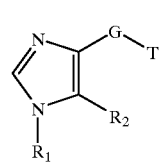

Formula I wherein $R_1$ is selected from the group consisting of H, —OCO—$R_7$, and —$C_2R_7$, with $R_7$ being a substituted or unsubstituted alkyl or aryl, the substituents on said substituted alkyl or aryl being selected from the group consisting of hydrogen, alkyl, alkenyl, alkynyl, aryl, aralkyl, cycloalkyl, heterocyclic and halogen;

$R_2$ is selected from the group consisting of H, hydroxyl or halogen;

G is a spacer moiety selected from the group consisting of a $C_3$–$C_7$ straight chain alkyl, a $C_2$–$C_7$ alkene or a $C_2$–$C_7$ alkyne, with said straight chain alkyl alkene or alkyne being optionally substituted with one or more $R_7$ groups; and T which represents a cyclic amine is a ring moiety selected from the group consisting of a, b, c or d below:

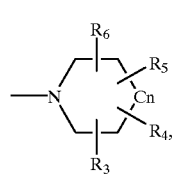

a

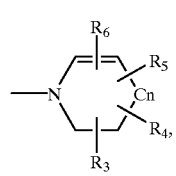

b

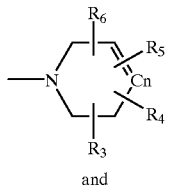

and

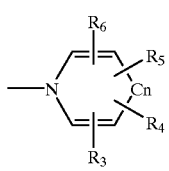

wherein n is an integer from 0–3, and $R_3$, $R_4$, $R_5$ and $R_6$ can be the same or different with the proviso that any two of said $R_3$, $R_4$, $R_5$ and $R_6$ can be bound to the same or different carbon atom of ring T, with said $R_3$, $R_4$, $R_5$ and $R_6$ being independently selected from the group consisting of H, substituted or unsubstituted $C_1$–$C_6$ alkyl, substituted or unsubstituted $C_1$–$C_6$ alkenyl, substituted or unsubstituted $C_1$–$C_6$ alkynyl, aryl, aralkyl, alkylaryl, cycloalkyl, heterocyclic, —C—O—$R_8$, —C(=O)$R_8$, —CO$_2R_8$, —OC(O)$R_8$, —NH$_2$, —NHR$_8$, —N($R_8$)$_2$, —NR$_8R_9$, —SR$_8$, —SO$_2R_8$, S(O)$R_8$, —OH, —OR$_8$, —CH$_2$OR$_8$, —CH$_2$NH$_2$, —CH$_2$N($R_8$)$_2$, —CH$_2$NHR$_8$, —CH$_2$SR$_8$, —C(O)—NHR$_8$, —C(O)NR$_8R_9$, —CN, —NO$_2$, —NR$_8$—CO—, —C(NH)—NR$_8$, —C(=NR$_8$)NR$_9$, —NR$_8$—C(NH)—, —NHR$_8$(CO)NHR$_9$, —(O—CR$_8$—CR$_8$—O)—, —CX($R_8$)$_2$, —CX$_2R_8$, —CX$_3$, —OCX$_3$, —N($R_8$)—S(O)$R_9$, —N($R_8$)—SO$_2R_9$, (=O), (=NH—OR$_8$), —C(=S)$R_8$, —NCR$_8$, —NOR$_8$, —NR$_8R_9$—SO$_2$—NR$_8R_9$, —OPO$_2R_8$, —P$^+$($R_8$)$_3$ $X^-$, —SO$_3$H, fused heteroaryl, and (=CR$_8$) wherein $R_8$ and $R_9$ are independently H or $C_1$–$C_6$ alkyl, aryl, aralkyl, alkylaryl, cycloalkyl or heterocyclic, and X is a halogen.

Preferred moieties for $R_1$ are hydrogen or a readily hydrolyzable group such as, for example, —O—CO—$R_7$, where $R_7$ is described above.

Preferred moieties for $R_2$ are hydrogen or halogen.

Preferred representatives of G are alkyl groups such as n-propyl, n-butyl as well as their isomers.

Preferred cyclic amine ring for T is a piperidine ring (n=1 in Formula I), as well as its 3,4-dehydro derivative, both being shown below:

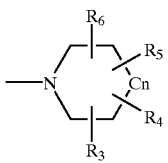 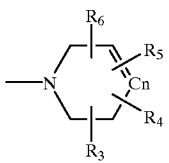

Preferred moieties for $R_3$, $R_4$, $R_5$ and $R_6$ are independently hydrogen, lower alkyl, —CO—NHR$_8$, —COOR$_8$, —CH$_2$NH—, —CH$_2$OH, —NH—, —CO—, —CH$_2$—NR$_9$—SO2—, as well as sets of two moieties that attach to the same carbon atom such as, for example, acetal. Representative compounds of the invention include:

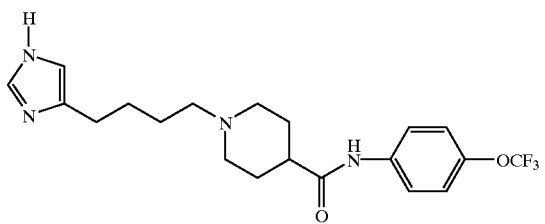

Formula II

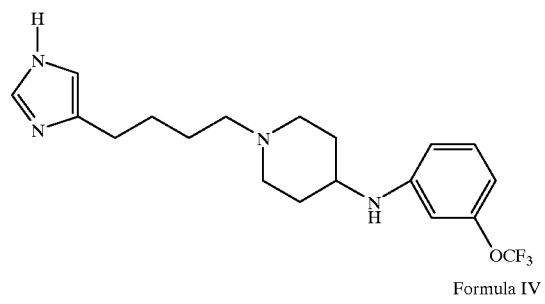

Formula III

Formula IV

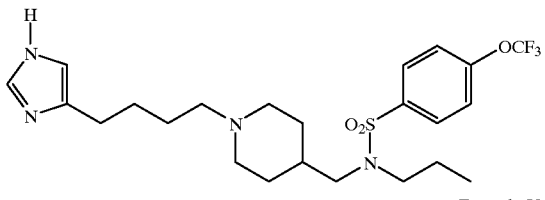

Formula V

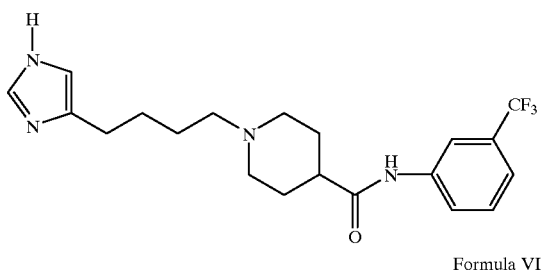

Formula VI

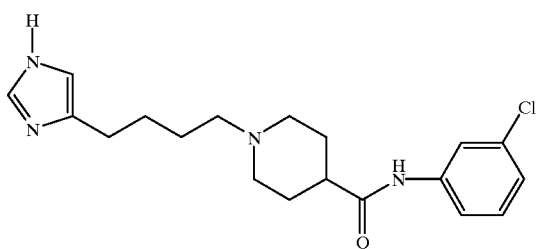

The compounds of the invention are basic and form pharmaceutically acceptable salts with organic and inorganic acids. Examples; of suitable acids for such salt formation are hydrochloric, sulfuric, phosphoric, acetic, citric, oxalic, malonic, salicylic, malic, fumaric, succinic, ascorbic, maleic, methanesulfonic and other mineral and carboxylic. acids well known to those skilled in the art. The salts are prepared by contacting the free base form with a sufficient amount of the desired acid to produce a salt in the conventional manner. The free base forms may be regenerated by treating the salt with a suitable dilute. aqueous base solution such as dilute aqueous sodium hydroxide, potassium carbonate, ammonia and sodium bicarbonate. The free base forms differ from their corresponding salt forms somewhat in certain physical properties, such as solubility in polar solvents, but the salts are otherwise equivalent to their corresponding free base forms for purposes of this invention.

Depending upon the substituents on the inventive compounds, one may be able to form salts with bases too. Thus, for example, if there are carboxylic acid substituents in the molecule, salts may be formed with inorganic as well as organic bases such as, for example, NaOH, KOH, $NH_4OH$, tetraalkylammonium hydroxide, and the like.

As stated earlier, the invention includes tautomers, enantiomers and other stereoisomers of the compounds also. Thus, as one skilled in the art knows, certain imidazoles may exist in tautomeric forms. Such variations are contemplated to be within the scope of the invention.

Another embodiment of the invention discloses a method of making the N-(imidazolylalkyl)-substituted cyclic amines disclosed above. The compounds may be prepared by several processes well known in the art. A preferred method may be exemplified by considering the imidazole-containing part of the molecule as the "left hand side" and the cyclic amine part as the "right hand side", the latter being illustrated, for convenience sake, as:

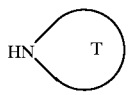

In a preferred process, the left hand side part is taken as an aldehyde compound which is condensed with the right hand side part to form a Schiffs base (an enamine). A catalyst is not usually necessary; however, if one is desired, materials such as, for example, triethylaluminum, molecular sieves (4é size, for example) may be used. Generally, this reaction is conducted in an organic solvent such as, for example, halogenated hydrocarbons, toluene, acetonitrile and the like, preferably in the absence of moisture, at temperatures in the range about 0–100° C., by bringing together the ingredients in contact in the solvent medium and stirring for about 10 minutes to about 48 hours at such temperatures. If the starting imidazole contains moieties such as, for example, NH, OH, $CO_2H$ and the like, such moieties are generally protected prior to the condensation reaction by using protecting groups such as, for example, triphenylmethyl, tert-butoxy, tert-butylester and the like, as is well known to those skilled in the art. The resulting Schiffs base may be isolated and reduced, or preferably reduced in situ, to the amine by treating with a suitable reductant such as, for example, sodium borohydride, sodium triacetoxyborohydride, sodium cyanoborohydride and the like, in an organic solvent at about 0–100° C. for about 0.1–48 hours. At a desired time, any protecting group may be deprotected. Thus, for example, if the protecting group is N-triphenylmethyl, deprotection may be accomplished by acid hydrolysis. The reaction steps may be depicted by the scheme:

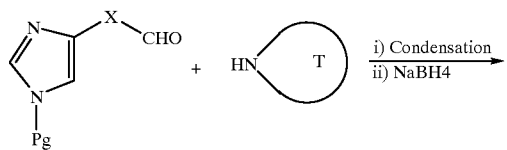

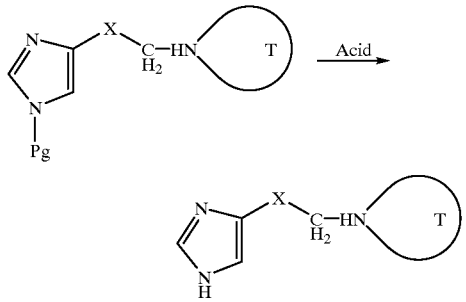

In the scheme above, PG represents a protecting group, and X represents (G-1) number of spacer moieties.

Isolation of the compound at various stages of the reaction may be achieved by standard techniques such as, for example, filtration, evaporation of solvent and the like. Purification of the product, intermediate and the like, may also be performed by standard techniques such as recrystallization, distillation, sublimation, chromatography, conversion to a suitable derivative which may be recrystallized and converted back to the amine, and the like. Such techniques are well known to those skilled in the art.

The thus prepared compounds may be analyzed for their composition and purity as well as characterized by standard analytical techniques such as, for example, elemental analysis, NMR, mass spectroscopy, and IR spectra.

The inventive compounds can readily be evaluated to determine activity at $H_3$ receptors by known methods, including, for example, the guinea pig brain membrane assay and the guinea pig neuronal ileum contraction assay, both of which are described in U.S. Pat. No. 5,352,707. Another useful assay utilizes rat brain membranes and is described by West et al. ("Identification of Two $H_3$-Histamine Receptor Subtypes", *Molecular Pharmacology*, (1990), Vol. 33, 610–613. Several of the present compounds were found to have high $H_3$ antagonist activity some of which are disclosed in the EXAMPLES section below.

In another embodiment, this invention provides pharmaceutical compositions comprising the above-described N-(imidazolylalkyl) substituted cyclic amines as an active ingredient. The pharmaceutical compositions generally additionally comprise a pharmaceutically acceptable carrier diluent, excipient or carrier (collectively referred to herein as carrier materials). Because of their $H_3$ antagonist activity, such pharmaceutical compositions possess utility in treating allergy, inflammation, nasal congestion, hypertension, glaucoma, sleeping disorders, states of hyper- and hypomotility of the gastrointestinal tract, hypo- and hyperactivity of the central nervous system, Alzheimers, Schizophrenia, migraines and the like diseases.

In yet another embodiment, the present invention discloses methods for preparing pharmaceutical compositions comprising the N-(imidazolylalkyl) substituted cyclic amines as an active ingredient. In the pharmaceutical compositions and methods of the present invention, the active ingredients will typically be administered in admixture with suitable carrier materials suitably selected with respect to the intended form of administration, i.e. oral tablets, capsules (either solid-filled, semi-solid filled or liquid filled), powders for constitution, oral gels, elixirs, dispersible granules, syrups, suspensions, and the like, and consistent with conventional pharmaceutical practices. For example, for oral administration in the form of tablets or capsules, the active drug component may be combined with any oral non-toxic pharmaceutically acceptable inert carrier, such as lactose, starch, sucrose, cellulose, magnesium stearate, dicalcium phosphate, calcium sulfate, talc, mannitol, ethyl alcohol (liquid forms) and the like. Moreover, when desired or needed, suitable binders, lubricants, disintegrating agents and coloring agents may also be incorporated in the mixture. Powders and tablets may be comprised of from about 5 to about 95 percent inventive composition. Suitable binders include starch, gelatin, natural sugars, corn sweeteners, natural and synthetic gums such as acacia, sodium alginate, carboxymethylcellulose, polyethylene glycol and waxes. Among the lubricants there may be mentioned for use in these dosage forms, boric acid, sodium benzoate, sodium acetate, sodium chloride, and the like. Disintegrants include starch, methylcellulose, guar gum and the like. Sweetening and flavoring agents and preservatives may also be included where appropriate. Some of the terms noted above, namely disintegrants, diluents, lubricants, binders and the like, are discussed in more detail below.

Additionally, the compositions of the present invention may be formulated in sustained release form to provide the rate controlled release of any one or more of the components or active ingredients to optimize the therapeutic effects, i.e. antihistaminic activity and the like. Suitable dosage forms for sustained release include layered tablets containing layers of varying disintegration rates or controlled release polymeric matrices impregnated with the active components and shaped in tablet form or capsules containing such impregnated or encapsulated porous polymeric matrices.

Liquid form preparations include solutions, suspensions and emulsions. As an example may be mentioned water or water-propylene glycol solutions for parenteral injections or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier such as inert compressed gas, e.g. nitrogen.

For preparing suppositories, a low melting wax such as a mixture of fatty acid glycerides such as cocoa butter is first melted, and the active ingredient is dispersed homogeneously therein by stirring or similar mixing. The molten homogeneous mixture is then poured into convenient sized molds, allowed to cool and thereby solidify.

Also included are solid form preparations which are intended to be converted, shortly before use, to liquid form preparations for either oral or parenteral administration. Such liquid forms include solutions, suspensions and emulsions.

The compounds of the invention may also be deliverable ransdermally. The transdermal compositions may take the form of creams, lotions, aerosols and/or emulsions and can be included in a transdermal patch of the matrix or reservoir type as a re conventional in the art for this purpose.

Preferably the compound is administered orally.

Preferably, the pharmaceutical preparation is in a unit dosage form. In such form, the preparation is subdivided into suitably sized unit doses containing appropriate quantities of the active components, e.g., an effective amount to achieve the desired purpose.

The quantity of the inventive active composition in a unit dose of preparation may be generally varied or adjusted from about 0.01 milligrams to about 1,000 milligrams, preferably from about 0.01 to about 950 milligrams, more preferably from about 0.01 to about 500 milligrams, and typically from about 1 to about 250 milligrams, according to the particular application. The actual dosage employed may be varied depending upon the patient's age, sex, weight and severity of the condition being treated. Such techniques are well known to those skilled in the art. Generally, the human oral dosage form containing the active ingredients can be administered 1 or 2 times per day. The amount and frequency of the administration will be regulated according to the judgment of the attending clinician. A generally recommended daily dosage regimen for oral administration may range from about 0.04 milligrams to about 4,000 milligrams per day, in single or divided doses.

Capsule—refers to a special container or enclosure made of methyl cellulose, polyvinyl alcohols, or denatured gelatins or starch for holding or containing compositions comprising the active ingredients. Hard shell capsules are typically made of blends of relatively high gel strength bone and pork skin gelatins. The capsule itself may contain small amounts of dyes, opaquing agents, plasticizers and preservatives.

Tablet—refers to a compressed or molded solid dosage form containing the active ingredients with suitable diluents. The tablet can be prepared by compression of mixtures or granulations obtained by wet granulation, dry granulation or by compaction.

Oral gels—refers to the active ingredients dispersed or solubilized in a hydrophillic semi-solid matrix.

Powders for constitution refers to powder blends containing the active ingredients and suitable diluents which can be suspended in water or juices.

Diluent—refers to substances that usually make up the major portion of the composition or dosage form. Suitable diluents include sugars such as lactose, sucrose, mannitol and sorbitol; starches derived from wheat, corn rice and potato; and celluloses such as microcrystalline cellulose. The amount of diluent in the composition can range from about 10 to about 90% by weight of the total composition, preferably from about 25 to about 75%, more preferably from about 30 to about 60% by weight, even more preferably from about 12 to about 60%.

Disintegrants—refers to materials added to the composition to help it break apart (disintegrate) and release the medicaments. Suitable disintegrants include starches; "cold water soluble" modified starches such as sodium carboxymethyl starch; natural and synthetic gums such as locust bean, karaya, guar, tragacanth and agar; cellulose derivatives such as methylcellulose and sodium carboxymethylcellulose; microcrystalline celluloses and cross-linked microcrystalline celluloses such as sodium croscarmellose; alginates such as alginic acid and sodium alginate; clays such as bentonites; and effervescent mixtures. The amount of disintegrant in the composition can range from about 2 to about 15% by weight of the composition, more preferably from about 4 to about 10% by weight.

Binders—refers to substances that bind or "glue" powders together and make them cohesive by forming granules, thus serving as the "adhesive" in the formulation. Binders add cohesive strength already available in the diluent or bulking agent. Suitable binders include sugars such as sucrose; starches derived from wheat, corn rice and potato; natural gums such as acacia, gelatin and tragacanth; derivatives of seaweed such as alginic acid, sodium alginate and ammonium calcium alginate; cellulosic materials such as methylcellulose and sodium carboxymethylcellulose and hydroxypropylmethylcellulose;

polyvinylpyrrolidone; and inorganics such as magnesium aluminum silicate. The amount of binder in the composition can range from about 2 to about 20% by weight of the composition, more preferably from about 3 to about 10% by weight, even more preferably from about 3 to about 6% by weight.

Lubricant—refers to a substance added to the dosage form to enable the tablet, granules, etc. after It has been compressed, to release from the mold or die by reducing friction or wear. Suitable lubricants include metallic stearates such as magnesium stearate, calcium stearate or potassium stearate; stearic acid; high melting point waxes; and water soluble lubricants such as sodium chloride, sodium benzoate, sodium acetate, sodium oleate, polyethylene glycols and d'l-leucine. Lubricants are usually added at the very last step before compression, since they must be present on the surfaces of the granules and in between them and the parts of the tablet press. The amount of lubricant in the composition can range from about 0.2 to about 5% by weight of the composition, preferably from about 0.5 to about 2%, more preferably from about 0.3 to about 1.5% by weight.

Glidents—materials that prevent caking and improve the flow characteristics of granulations, so that flow is smooth and uniform. Suitable glidents include silicon dioxide and talc. The amount of glident in the composition can range from about 0.1% to about 5% by weight of the total composition, preferably from about 0.5 to about 2% by weight.

Coloring agents—excipients that provide coloration to the composition or the dosage form. Such excipients can include food grade dyes and food grade dyes adsorbed onto a suitable adsorbent such as clay or aluminum oxide. The amount of the coloring agent can vary from about 0.1 to about 5% by weight of the composition, preferably from about 0.1 to about 1%.

Bioavailability—refers to the rate and extent to which the active drug ingredient or therapeutic moiety is absorbed into the systemic circulation from an administered dosage form as compared to a standard or control.

Conventional methods for preparing tablets are known. Such methods include dry methods such as direct compression and compression of granulation produced by compaction, or wet methods or other special procedures. Conventional methods for making other forms for administration such as, for example, capsules, suppositories and the like are also well known.

Another embodiment of the invention discloses use of the pharmaceutical compositions disclosed above for treatment of diseases such as, for example, allergy, inflammation, nasal congestion, hypertension, glaucoma, sleeping disorders, states of hyper- and hypo-motility of the gastrointestinal tract, hypo- and hyperactivity of the central nervous system, Alzheimers, Schizophrenia, migraines and the like. The method (comprises administering a therapeutically effective amount of the inventive pharmaceutical composition to a patient having such a diseases or diseases and in need of such a treatment.

In a still another embodiment, this invention discloses pharmaceutical compositions comprising the inventive N-(imidazolylalkyl) substituted cyclic amine compound in combination with a histamine-$H_1$ receptor antagonist. Optionally there may be a suitable pharmaceutically acceptable carrier present. Numerous chemical substances are known to have histamine-$H_1$ receptor antagonist activity. Many such compounds can be classified broadly as ethanolamines, ethylenediamines, alkylamines, phenothiazines, piperidines, and the like. Illustrative $H_1$ receptor antagonists useful in the practice of the present invention include, without limitation, astemizole, azatadine, azelastine, acrivastine, brompheniramine, chlorpheniramine, clemastine, cyclizine, carebastine, cyproheptadine, carbinoxamine, descarboethoxyloratadine (also known as desloratadine or "DCL"), doxylamine, dimethindene, ebastine, epinastine, efletirizine, fexofenadine, hydroxyzine, ketotifen, loratadine, levocabastine, meclizine, mizolastine, mequitazine, mianserin, noberastine, norastemizole, picumast, pyrilamine, promethazine, terfenadine, tripelennamine, temelastine, trimeprazine, and tripolidine. Other compounds can readily be evaluated to determine activity at $H_1$ receptors by known methods including, for example, specific blockade of the contractile response to histamine of isolated guinea pig ileum. All such $H_1$ receptor antagonists are suitable to prepare the pharmaceutical compositions.

Yet another embodiment of the invention discloses methods for preparing pharmaceutical compositions comprising the N-(imidazolylalkyl) substitute cyclic amines and a histamine-$H_1$ receptor antagonist. And a still another embodiment discloses the aspect of using such compositions for treatment of allergy-induced airway (e.g. upper airway) responses. Those skilled in the art will realize that the term "upper airway" means the upper respiratory system—i.e., the nose, throat, and associated structures.

It will be apparent to those skilled in the art that many modifications, variations and alterations to the present disclosure, both to materials and methods, may be practiced. Such modifications, variations and alterations are intended to be within the spirit and scope of the present invention.

The following EXAMPLES are being provided to further illustrate the present invention. They are for illustrative purposes only; the scope of the invention is not to be considered limited in any way thereby.

EXAMPLES

Unless otherwise stated, the following abbreviations have the stated meanings in the Examples below:

DBU=1,8-diazabicyclo[5.4.0]undec-7-ene

DBN=1,5-diazabicyclo[4.3.0]non-5-ene

EDCI=1-(3-dimethylaminopropyl)-3-ethylcarbodiimide

HOBT=1-hydroxybenzotriazole

DCC=dicyclohexylcarbodiimide

Dibal-H=diisobutylaluminum hydride

LAH=lithium aluminum hydride

NaBH(OAc)$_3$=sodium triacetoxyborohydride

NaBH$_4$=sodium borohydride

NaBH$_3$CN=sodium cyanoborohydride

LDA=lithium diisopropylamide p-TsOH=p-toluenesulfonic acid

TMAD=N,N,N',N'-tetramethylazodicarboxamide

CSA=camphorsulfonic acid

HRMS=High Resolution Mass Spectrometry

HPLC=High Performance Liquid Chromatography

LRMS=Low Resolution Mass Spectrometry nM=nanomolar

Ki=Dissociation Constant of Enzyme-inhibitor complex pA2=-logEC$_{50}$, as defined by J. Hey, *Eur. J. Pharmacol.*, (1995), Vol. 294, 329.

Ci/mmol=Curie/mmol (a measure of specific activity)

Tr=Triphenylmethyl

Tris=Tris(hydroxymethyl)aminomethane

Example 1

Preparation of a Compound of Formula I with R$_1$= triphenylmethyl, R$_2$=R$_4$=R$_5$=R$_6$=H, G=4, n=1, and R$_3$=CO$_2$Et (i) Preparation of 1-triphenylmethyl-4-(4-butylcarboxaldehyde) imidazole:

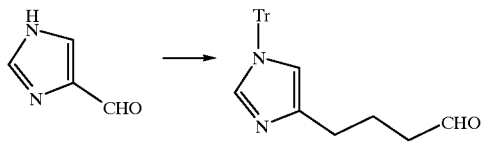

To a solution of commercially available 4-imidazolecarboxaldehyde (50 g, 0.52 mol) and triethylamine (190 mL) in methylene chloride (500 mL) was added triphenylmethyl chloride (175 g, 63 mol) in portions over 1.5 h. After 24 h the reaction was filtered, and the filtrate concentrated to approximately 300 mL. The organic phase was washed with water, 1 M NaOH, saturated brine, dried over MgSO4 and concentrated in vacuo to a semi-solid. Recrystallization from hexanes-ethyl acetate afforded pure with 1-trityl imidazolecarboxaldehyde (55 g).

A 1 liter flask was charged with 1-trityl imidazolecarboxaldehyde (10 g, 29.6 mmol), THF (dry, 500 ml) and 3-benzyloxypropyl triphenylphosphonium bromide (15.3 g, 31.1 mmol) and cooled to –10° C. Potassium t-Butoxide (1 M in dioxane, 31.2 mL) was added dropwise over 10 min and the reaction allowed to warm slowly to room temperature. After 4 h the reaction was filtered through celite, partially concentrated, ethyl acetate added and the organic layer washed with water. The organic layer was dried and concentrated to afford crude product.

A 500 mL hydrogenation vessel was charged with the crude product above (~11.5 g), methanol (60 mL), 10% palladium on carbon (1.0 g) and was shaken under hydrogen gas (55 psi) for 20 h. The catalyst was removed by filtration through celite and the product purified by chromatography on silica using methanol/methylene chloride eluent to afford 7.2 g with 4-hydroxypropyl 1-trityl imidazole.

A 500 mL flask was charged with methylene chloride, DMSO ((6 g, 76 mmol) and cooled to –65° C. Oxalyl chloride ((7.2 g, 57 mmol) was added in three portions over 10 min. After 10 min., 4-hydroxypropyl-1-trityl imidazole (7.2 g, 19 mmol) was added as a solution in methylene chloride. After 5 min triethyl amine (9.6 g, 95 mmol) was added and the reaction allowed to warm slowly and stir overnight. The reaction was quenched with 1M potassium hydrogen phosphate, washed with water and the organic layer concentrated to crude aldehyde (5.7 g).

(ii) Preparation of a compound of Formula I with R$_1$=triphenylmethyl, R$_2$=R$_4$=R$_5$=R$_6$=H, G=4, n=1, and R$_3$=CO$_2$Et:

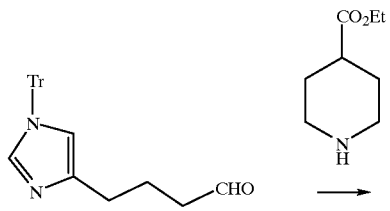

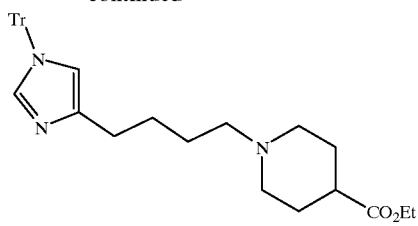

To a 1,2-dichloroethane solution (15 ml) of 1-triphenylmethyl-4-(4-butylcarbcxaldehyde) imidazole (1.66 mg, 4.37 mmol) was added ethyl isonipecotate (0.84 ml, 5.45 mmol) followed by sodium triacetoxyborohydride (1.39 g, 6.56 mmol) at room temperature. The mixture was stirred for 24 h under nitrogen and then quenched with water. Sodium hydroxide (5% aq.) was added and the layers were separated. The combined organic layers were washed with brine, dried over MgSO$_4$, filtered arid concentrated. The crude product was chromatographed on silica gel eluting with 2% MeOH—CH$_2$Cl$_2$ increasing gradually to 10% MeOH in CH2Cl2. The product was obtained (2.03 g, 89%) as a clear oil which solidified on standing. LRMS (Cl, M+H)=522.

Example 2

Deprotection of the product from Example 1

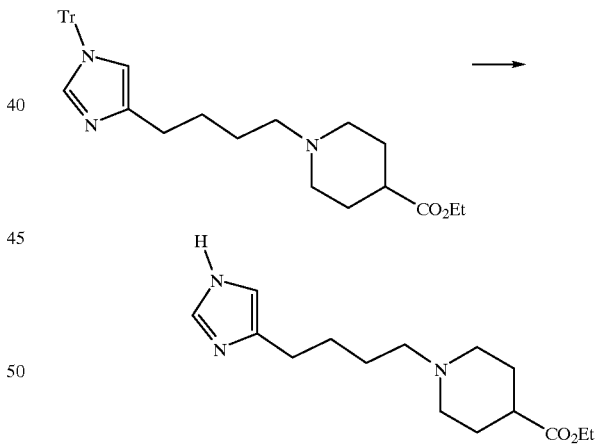

To a dioxane solution (3 ml) of the trityl protected imidazole (170 mg, 0.330 mmol) was added a 4M HCl-dioxane solution (0.65 ml) at room temperature. The mixture was heated to 80° C. for 4 h, at which time the hydrochlorice salt precipitated out of solution as a gum covering the walls of the flask. The mixture was cooled to room temperature, and the solvent was decanted from the gummy residue. The residue was rinsed consecutive y with Et$_2$O, EtOAc and CH$_2$Cl$_2$ and dried under vacuum to provide the desired material as a light brown gum. LRMS (Cl, M+H)=280.

Example 3

Preparation of compound according to the reaction

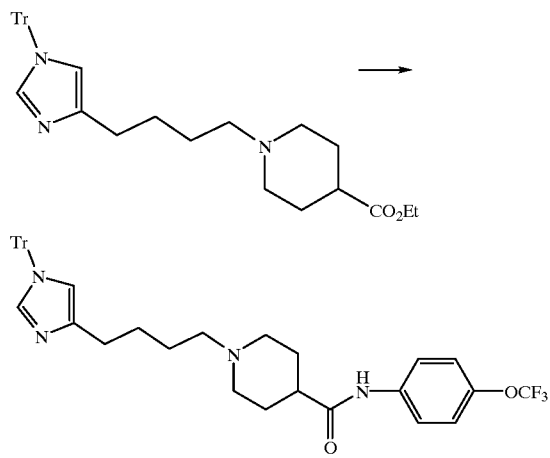

Trifluoromethoxyaniline (0.0285 ml, 0.211 mmol) was mixed with anhydrous $CH_2Cl_2$ (1 ml) in a dry flask. Trimethyl aluminum (0.315 ml, 0.633 mmol) was added via syringe, and the reaction mixture was stirred at room temperature for 15 min. A $CH_2Cl_2$ solution of ester (100 mg, 0.192 mmol) was then added and stirring was continued for 48 h. The reaction was quenched carefully with $H_2O$ and MeOH, filtered through celite, and concentrated. Chromatography on silica gel eluting with 100% $CH_2Cl_2$ increasing gradually to 10% MeOH—$CH_2Cl_2$ afforded 94 mg (75%) of the desired material. LRMS (Cl, M+H)=653. Analytical CHN for ($C_{39}H_{39}N_4O_2F_3$): C, 69.65; H, 6.17; N, 8.33: Found C, 69.55; H, 6.19; N, 8.25.

Example 4

Preparation of compound of Formula II according to the reaction

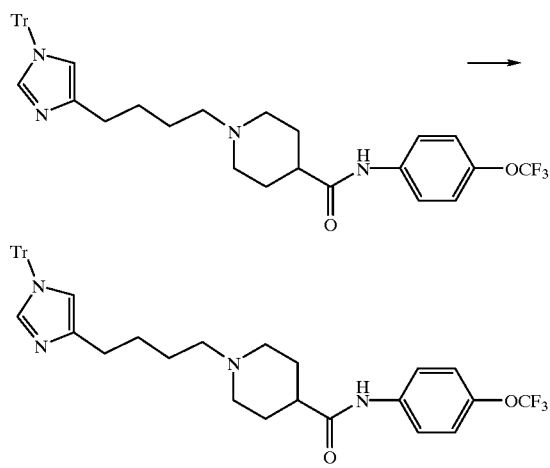

The trityl compound (162 mg, 0.248 mmol) was taken as a dioxane solution (3 ml). 4M HCl-dioxane solution (0.5 ml) was added and reacted as above. The product was obtained as a light brown gum. LRMS (Cl, M+H)=411. HRMS calc. 411.2008; Found 411.2011.

Example 5

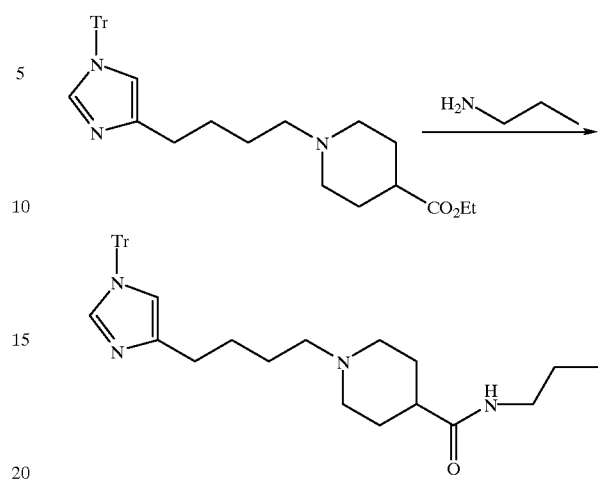

n-Propylamine (0.226 ml, 2.76 mmol) was mixed with anhydrous toluene (10 ml) in a dry flask. Trimethyl aluminum (4.2 ml, 8.3 mmol) was added via syringe, and the reaction mixture was stirred at room temperature for 15 min. A toluene solution of the ester (1.3 g, 2.51 mmol) was then added and stirring was continued for 24 h at 60° C. The reaction was cooled to room temperature and quenched carefully with $H_2O$ and MeOH, filtered through celite, and concentrated. Chromatography on silica gel eluting with 100% $CH_2Cl_2$ increasing gradually to 10% MeOH—$CH_2Cl_2$ afforded 1.28 g (95%) of the desired product. LRMS (Cl, M+H)=535. Analytical CHN for ($C_{35}H_{42}N_4O \times 0.8$ $H_2O$): C, 76.55; H, 8.00; N, 10.20: Found C, 76.76; H, 7.99; N, 10.21.

Example 6

Reduction of the Amide to Amine

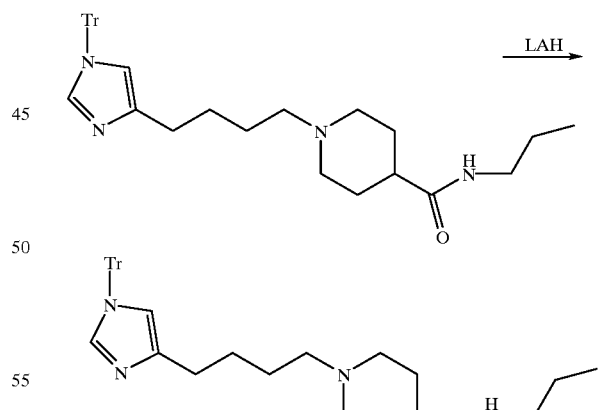

To a mixture of LAH (274 mg, 7.2 mmol) in freshly distilled THF (12 ml) was added a THF solution of the amide (1.27 g, 2.38 mmol) at room temperature). The mixture was then heated to reflux for 3.5 hr., then cooled to room temperature and quenched with solid $Na_2SO_4 \times 10\ H_2O$, and 2.5M NaOH (0.5 ml). The slurry was filtered through celite and the filtrate was concentrated and chromatographed on silica gel (30 g) eluting with 10% MeOH—$CH_2Cl_2$ increasing to 10% MeOH—CH$_2$Cl$_2$ containing 1% NH$_4$OH, afforded 904 mg (73%) of product. LRMS (Cl, M+H)=521. HRMS calc. 521.3644; found 521.3643.

Example 7

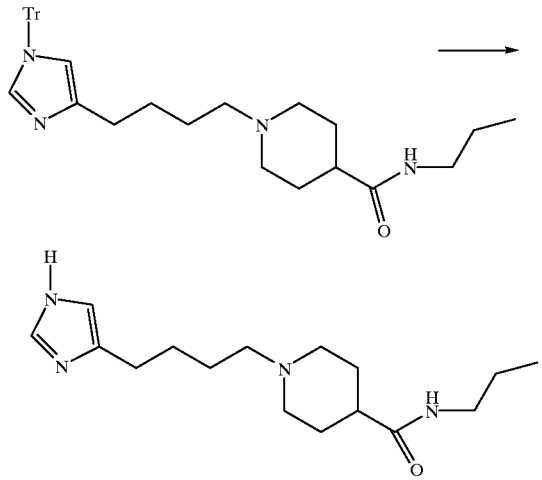

To a dioxane solution (3 ml) of the trityl precursor (117 mg, 0.219 mmol) was added 4M HCl-dioxane solution (0.5 ml) and reacted as above The deprotected amide was obtained as a light brown gum. LRMS (Cl, M+H)=293. HRMS calc. 293.2341; Found 293.2339.

Example 8

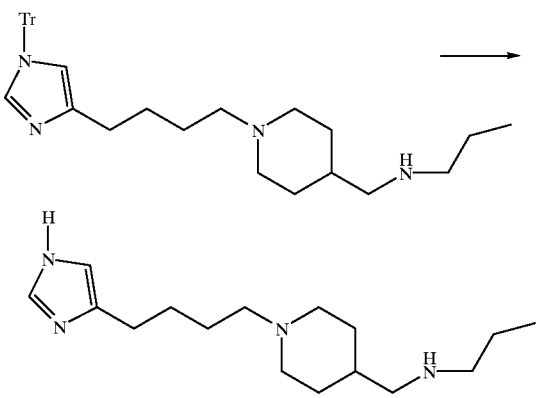

To a dioxane solution (3 ml) of the trityl precursor (270 mg, 0.519 mmol) was added 4M HCl-dioxane solution (1.5 ml) and reacted as above. The product was obtained as a light brown gum. LRMS (Cl, M+H) =279. HRMS calc. 279.2549; Found 279.2549.

Example 9

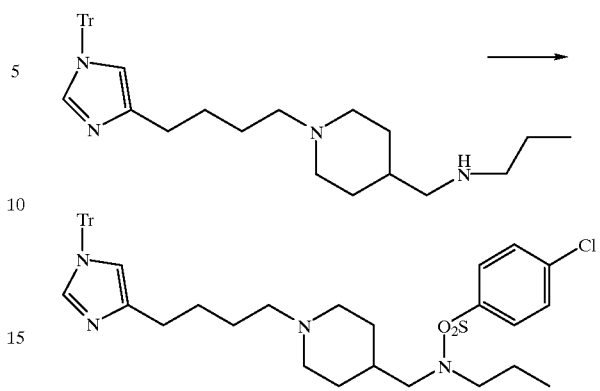

To a CH$_2$Cl$_2$ (3 ml) containing Et$_3$N (0.217 ml, 1.56 mmol) and the imidazolylamine (270 mg, 0.520 mmol) was added 4-chlorobenzenesulfonyl chloride (108 mg, 0.510 mmol). The mixture was stirred at rcom temperature for 24 h, then concentrated, and chromatographed directly on silica gel (25 g) eluting with 5% MeOH—CH2Cl2 increasing to 5% MeOH—CH$_2$Cl$_2$ containing 1% NH$_4$OH which afforded 272 mg (77%) of pure material. LRMS (Cl, M+H)= 695. Analytical CHNS for (C$_{41}$H$_{45}$N$_4$O$_2$SCl×0.7 H$_2$O): C, 69.56; H, 6.89; N, 7.91; S, 4.53: Found C, 63.53; H,7.09; N, 7.72; S, 4.36.

Example 10

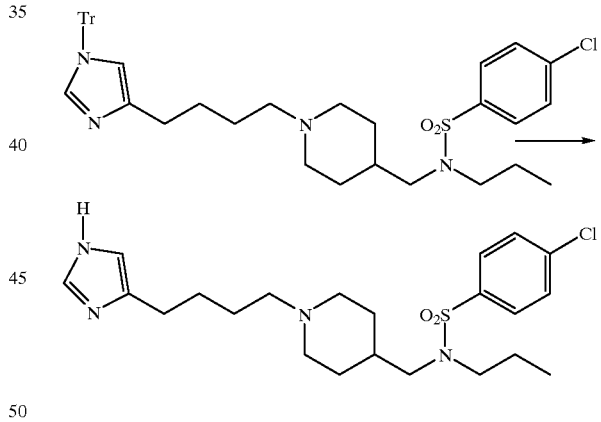

To a dioxane solution (3 ml) of the trityl precursor (192 mg, 0.277 mmol) was added 4M HCl-dioxane solution (0.6 ml) and reacted as above. The product was obtained as a light brown gum. LRMS (Cl, M+H) =453.

Example 11

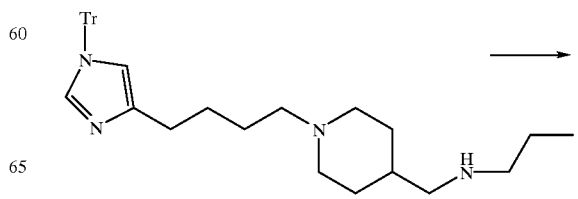

-continued

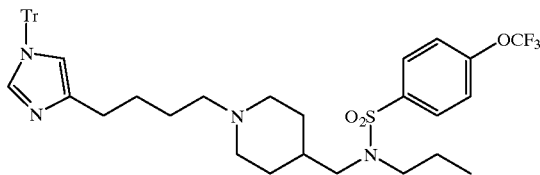

To a CH$_2$Cl$_2$ (3 ml) containing Et$_3$N (0.217 ml, 1.56 mmol) and the amine (270 mg, 0.520 mmol) was added 4-trifluoromethoxybenzene sulfonyl chloride (0.088 ml, 0.510 mmol). The mixture was stirred at room temperature for 24 h, then concentrated, and chromatographed directly on silica gel (25 g) eluting with 5% MeOH—CH2Cl$_2$ increasing to 5% MeOH-CH$_2$Cl$_2$ containing 1% NH$_4$OH which afforded 171 mg (45%) of pure material. LRMS (Cl, M+H)=745. HRMS calc for (C$_{42}$H$_{47}$N$_4$O$_3$SF$_3$) 745.3399; Found 745.3417.

Example 12

Preparation of compound of Formula IV

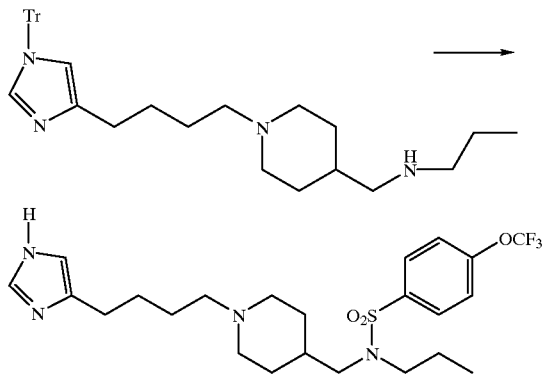

To a dioxane (3 ml) solution of the trityl precursor (136 mg, 0.183 mmol) was added 4M HCl-dioxane solution (0.6 ml) and reacted as above. The product was obtained as a light brown gum. LRMS (Cl,M+H)=503.

Example 13

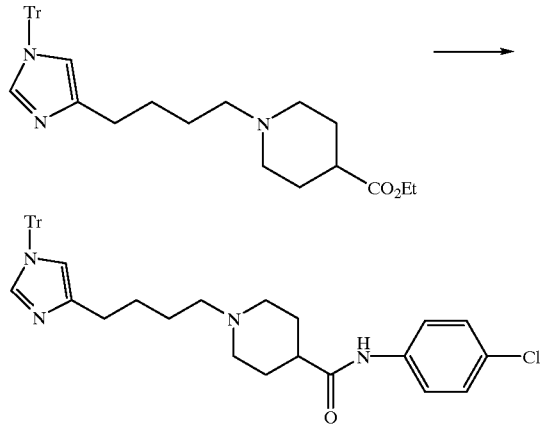

To the starting ester (500 mg, 0.959 mmol) were added p-chloroaniline (145 mg, 1.13 mmol), toluene (5 ml), trimethylaluminum (2.0 ml, 4.0 mmol) and reacted as above. The product was obtained (486 mg, 83%) as a faint yellow solid. LRMS (Cl, M+H)=603.

Example 14

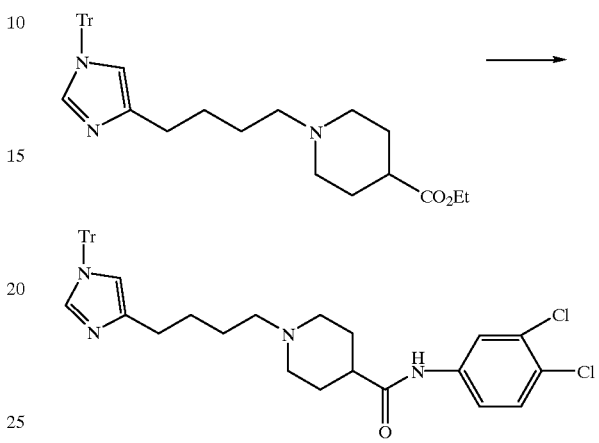

To the ester (500 mg, 0.959 mmol) were added 3,4-dichloroaniline (190 mg, 1.17 mmol), toluene (5 ml), trimethylaluminum (2.0 ml, 4.0 mmol) and reacted as above. The product was obtained (530 mg, 87%) as a faint amber solid. LRMS (Cl, M+H)=637.

Example 15

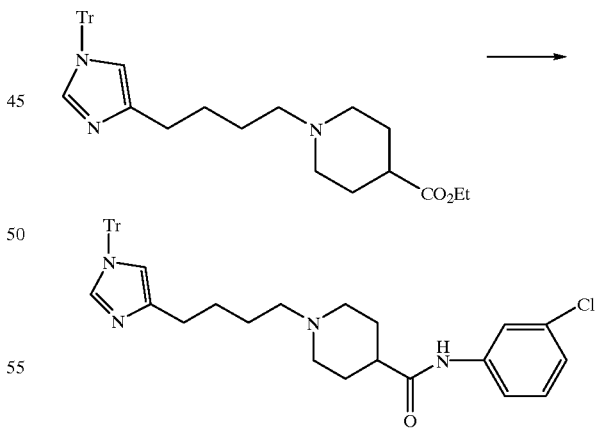

To the ester (500 mg, 0.959 mmol) were added m-dichloroaniline (150 mg, 1.18 mmol), toluene (5 ml), trimethylaluminum (2.0 ml, 4.0 mmol) and reacted as above. The product was obtained (557 mg, 96%) as an off white foam. LRMS (Cl, M+H)=603.

Example 16

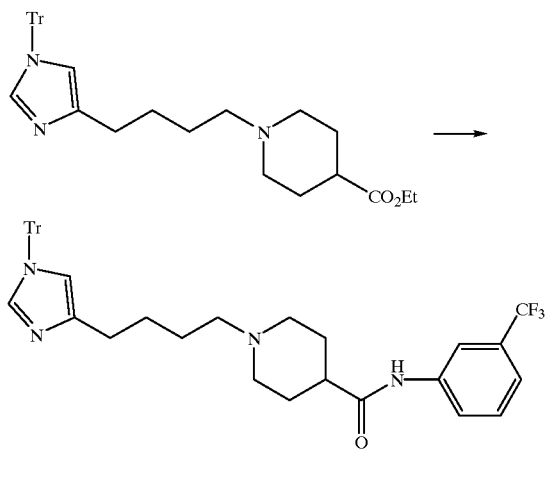

To the ester (500 mg, 0.959 mmol) were added 3-trifluoromethylaniline (185 mg, 1.15 mmol), toluene (5 ml), trimethylalliminum (2.0 ml, 4.0 mmol) and reacted as above. The product was obtained (533 mg, 88%) as an off white solid. MP=145–148° C. LRMS (Cl, M+H)=637.

Example 17

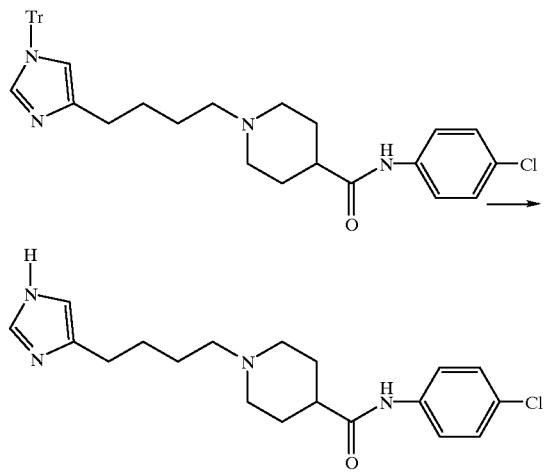

To a dioxane solution (6 ml) of the trityl precursor (160 mg, 0.266 mmol) was added a 4M HCl-dioxane solution (0.5 ml) at room temperature. The mixture was heated to 80° C. for 4 h, at which time the hydrochloride salt precipitated out of solution as a gum covering the walls of the flask. The mixture was cooled to room temperature, and the solvent was decanted from the gummy residue. The residue was rinsed consecutively with $Et_2O$, EtOAc and $CH_2Cl_2$ and dried under vacuum to provide 92 mg of the product as a light brown gum. LRMS (Cl, M+H)=361.

Example 18

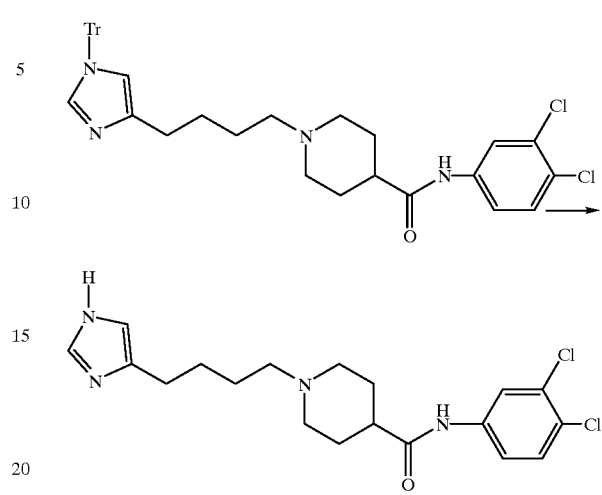

Using the same procedure as in Example 17, the trityl precursor (200 mg, 0.314 mmol) in dioxane (6 ml) was deprotected using 4M HCl-dioxane 0.5 ml). The product was obtained (138 mg) as a brown gum. LRMS (Cl, M+H)= 395.

Example 19

Preparation of compound of Formula VI

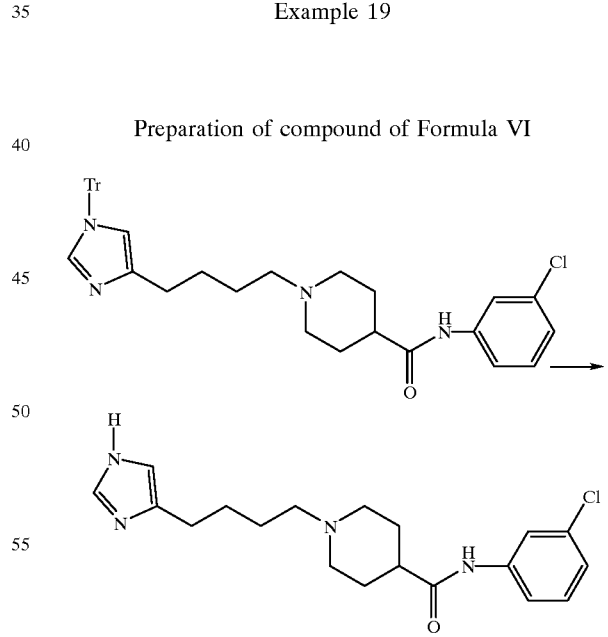

By using a similar procedure as in Example 17, the trityl precursor (200 mg, 0.332 mmol) in dioxane (6 ml) was deprotected using 4M HCl-dioxane (0.5 ml) to yield 126 mg of product as an amber foam. LRMS (Cl, M+H)=361.

Example 20

Preparation of compound of Formula V

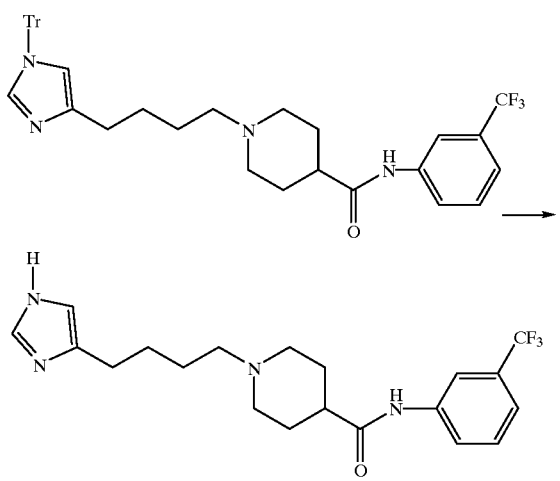

By using a similar procedure as in Example 17, the trityl precursor (200 mg, 0.332 mmol), in dioxane (6 ml) was deprotected using 4M HCl-dioxane (1.0 ml) to yield 183 mg of product as an amber foam. LRMS (Cl, M+H)=395.

General Procedure for $H_3$-Receptor Binding Assay

The source of the $H_3$ receptors in this experiment was guinea pig brain. The animals weighed 400–600 g. The brain tissue was homogenized with a solution of 50 mM Tris, pH 7.5. The final concentration of tissue in the homogenization buffer was 10% w/v. The homogenates were centrifuged at 1,000× g for 10 min. in order to remove clumps of tissue and debris. The resulting supernatants were then centrifuged at 50,000× g for 20 min. in order to sediment the membranes, which were next washed three times in homogenization buffer (50,000× g for 20 min. each). The membranes were frozen and stored at −70° C. until needed.

All compounds to be tested were dissolved in DMSO and then diluted into the binding buffer (50 mM Tris, pH 7.5) such that the final traction was 2 μg/ml with 0.1% DMSO. Membranes were then added (400 μg of protein) to the reaction tubes. The reaction was started by the addition of 3 nM [$^3$H]R-α-methylhistamine (8.8 Ci/mmol) or 3 nM [$^3$H] $N^α$-methylhistamine (80 Ci/mmol) and continued under incubation at 30° C. for 30 min. Bound ligand was separated from unbound ligand by filtration, and the amount of radioactive ligand bound to the membranes was quantitated by liquid scintillation spectrometry. All incubations were performed in duplicate and the standard error was always less than 10%. Compounds that inhibited more than 70% of the specific binding of radioactive ligand to the receptor were serially diluted to determine a $K_i$ (nM). The results are given in the Table 1 for the HCl salt of the indicated compound.

TABLE 1

| No. | G | T | R | Ki | pA2 |
|---|---|---|---|---|---|
| 1 | $(CH_2)_4$ | a | —COOEt | 22 | |
| 2 | $(CH_2)_4$ | a | 4-CONH-Ph-4-OCF$_3$ (Example 4) | 2 | 9.3 |
| 3 | $(CH_2)_4$ | a | 4-CO-NH-Propyl (Example 7) | 53 | |
| 4 | $(CH_2)_4$ | a | 4-CH$_2$-NH-Propyl (Example 8) | 200 | |
| 5 | $(CH_2)_4$ | a | 4-CH$_2$-NH-(SO$_2$-Ph-4-Cl)-propyl (Example 10) | 44 | |
| 6 | $(CH_2)_4$ | a | 4-CH$_2$-NH-(SO$_2$-Ph-4-OCF$_3$)-propyl (Example 12) | 24 | 6.5 |
| 7 | $(CH_2)_4$ | a | 4-CONH-Ph-4-Cl (Example 17) | 35 | |
| 8 | $(CH_2)_4$ | a | 4-CONH-Ph-3,4-Cl (Example 18) | 27 | 6.8 |
| 9 | $(CH_2)_4$ | a | 4-CONH-Ph-3-Cl (Example 19) | 5.5 | 8.9 |
| 10 | $(CH_2)_4$ | a | 4-CONH-Ph-3-CF$_3$ | 9 | 9.1 |
| 11 | $(CH_2)_3$ | a | 4-CONH-Ph-3-OCF$_3$ | 1 | 9.2 |
| 12 | $(CH_2)_3$ | a | 4-CONH-CH$_2$Ph-4-Cl | 29 | 8 |
| 13 | $(CH_2)_3$ | a | 4-CONH-CH$_2$Ph-4-OCF$_3$ | 24 | 7.5 |
| 14 | $(CH_2)_3$ | a | 4-CONH-Ph-4-OBu | 10 | 9 |
| 15 | $(CH_2)_3$ | a | 4-CONH-Ph-4-OH | 100 | |
| 16 | $(CH_2)_3$ | a | 4-CONH-Ph-3-OH | 700 | |
| 17 | $(CH_2)_3$ | a | 4-NHCO-Ph-4-OCF$_3$ | 23 | |
| 18 | $(CH_2)_3$ | a | 4-NHCO-Ph-4-F | 52 | |
| 19 | $(CH_2)_4$ | a | 4-CH$_3$; 4-CONH-Ph-4-OCF$_3$ | 180 | 7.4 |
| 20 | $(CH_2)_4$ | a | 3-CH$_3$; 3-CONH-Ph-4-OCF$_3$ | 170 | |
| 21 | $(CH_2)_4$ | a | 4-NH-CH$_2$Ph-4-OCF$_3$ | 13 | 8.1 |
| 22 | $(CH_2)_4$ | a | 4-CH$_2$NH-Ph-4-OCF$_3$ | 9 | |
| 23 | $(CH_2)_4$ | a | 4-NH-Ph-3-OCF$_3$ | 7 | 8.1 |
| 24 | $(CH_2)_4$ | a | 4-N-piperidine | 100 | 6.2 |
| 25 | $(CH_2)_3$ | a | 4-OH; 4-Ph-4-Cl | 6 | 7.9 |
| 26 | $(CH_2)_4$ | a | 4-OH; 4-Ph-4-Cl | 6 | 8 |
| 27 | $(CH_2)_5$ | a | 4-OH; 4-Ph-4-Cl | 5 | 8.1 |
| 28 | $(CH_2)_4$ | a | 4-OH; 4-Ph-3-CF$_3$ | 60 | |
| 29 | $(CH_2)_3$ | a | 4-(CH$_2$)$_3$-4-piperidinyl-(CH$_2$)$_2$-OH | 12 | 7.1 |
| 30 | $(CH_2)_4$ | a | 4-(CH$_2$)$_3$-4-piperidinyl-(CH$_2$)$_2$-OH | 7 | 7.7 |
| 31 | $(CH_2)_4$ (3,4-dihydro) | c | 4-Ph-4-F | 14 | 7.9 |
| 32 | $(CH_2)_3$ | a | 4-CO-Ph-4-F | 6 | 7.7 |
| 33 | $(CH_2)_4$ | a | 4-CO-Ph-4-F | 3 | 8.2 |
| 34 | $(CH_2)_4$ | a | 4-CH$_2$-OPh-4-F | 10 | 7.7 |
| 35 | $(CH_2)_3$ | a | 4-Ph, 4-COEt | 500 | |
| 36 | $(CH_2)_3$ | a | 4-OH, 4-CH2Ph | 660 | |

From these test results and the background knowledge about the compounds described in the references in the section "Background of the invention", it would be apparent to the skilled artisan that the compounds of the invention would be useful in treating inflammation, allergy, diseases of the Gl-tract, cardiovascular disease, disturbances of the central nervous system and the like diseases stated earlier.

The following Example A and Example B illustrate, in a non-limiting way, the preparation of pharmaceutical dosage forms which contain a compound of the invention. As used therein, the term "active compound" is used to designate one of the compounds of Formula I or salt thereof.

PHARMACEUTICAL DOSAGE FORM EXAMPLES

EXAMPLE A

Tablets

| No. | Ingredients | mg/tablet | mg/tablet |
|---|---|---|---|
| 1 | Active compound | 100 | 500 |
| 2 | Lactose USP | 122 | 113 |
| 3 | Corn Starch, Food Grade, as a 10% paste in Purified Water | 30 | 40 |
| 4 | Corn Starch, Food Grade | 45 | 40 |
| 5 | Magnesium Stearate | 3 | 7 |
|   | Total | 300 | 700 |

General Method of Manufacture

Items No. 1 and 2 are mixed in a suitable mixer for about 10 to 15 minutes. The mixture is then granulated with Item No. 3. The damp granules are milled through a coarse screen (e.g., ¼", 0.63 cm) if necessary. The damp granules are then dried. The dried granules are screened if necessary and then mixed with Item No. 4 for about 10–15 minutes. Item No. 5 is then added and mixed for about 1 to 3 minutes. The mixture is then compressed to the appropriate size and weight on a suitable tablet machine.

EXAMPLE B

Capsules

| No. | Ingredient | mg/capsule | mg/capsule |
|---|---|---|---|
| 1 | Active compound | 100 | 500 |
| 2 | Lactose USP | 106 | 123 |
| 3 | Corn Starch, food grade | 40 | 70 |
| 4 | Magnesium stearate, NF | 4 | 7 |
|   | Total: | 250 | 700 |

General Method of Manufacture

Items No. 1, 2 and 3 are mixed in a suitable blender for about 10 to 15 minutes. Item No. 4 is then added and mixed for about 1 to 3 minutes. The mixture is filled into suitable two-piece hard gelatin capsules on a suitable encapsulating machine.

What is claimed is:

1. A compound, including enantiomers, stereoisomers and tautomers thereof, or pharmaceutically acceptable salts or solvates of said compound, said compound having the formula:

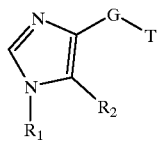

wherein $R_1$ is selected from the group consisting of H, —OCO—$R_7$, and —$CO_2R_7$, with $R_7$ being a substituted or unsubstituted alkyl or aryl, the substituents on said substituted alkyl or aryl being selected from the group consisting of hydrogen, alkyl, alkenyl, alkynyl, aryl, aralkyl, cycloalkyl, and halogen;

$R_2$ is selected from the group consisting of H, hydroxyl or halogen;

G is a spacer moiety selected from the group consisting of a $C_3$–$C_7$ straight chain alkyl, a $C_2$–$C_7$ alkene or a $C_2$–$C_7$ alkyne, with said straight chain alkyl, alkene or alkyne being optionally substituted with one or more $R_7$ groups; and T which represents a cyclic amine is a ring moiety of structure a below:

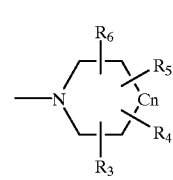

wherein n is an integer from 0–3, and $R_3$, $R_4$, $R_5$ and $R_6$ can be the same or different and are independently selected from the group consisting of H, substituted or unsubstituted $C_1$–$C_6$ alkyl, substituted or unsubstituted $C_1$–$C_6$ alkenyl, substituted or unsubstituted $C_1$–$C_6$ alkynyl, aryl, aralkyl, alkylaryl, cycloalkyl, Z-Pyridyl, —C—O—$R_8$, —C(=O)$R_8$, —$CO_2R_8$, —OC(O)$R_8$, —$NH_2$, —$NHR_8$, —N($R_8$)$_2$, —$NR_8R_9$, —$SR_8$, —$SO_2R_8$, —S(O)$R_8$, —OH, —$OR_8$, —$CH_2OR_8$, —$CH_2NH_2$, —$CH_2N(R_8)_2$, —$CH_2NHR_8$, —$CH_2SR_8$, —C(O)—$NHR_8$, —C(O)$NR_8R_9$, —CN, —$NO_2$, —C(NH)—$NR_8$, —C(=$NR_8$)$NR_9$, —$NHR_8$(CO)$NHR_9$, —CX($R_8$)$_2$, —$CX_2R_8$, —$CX_3$, —$OCX_3$, —N($R_8$)—S(O)$R_9$, —N($R_8$)—$SO_2R_9$, —C(=S)$R_8$, —$NCR_8$, —$NOR_8$, —$NR_8R_9$—$SO_2$—$NR_8R_9$, —$OPO_2R_8$, —$P^+(R_8)_3$ $X^-$, and —$SO_3H$, wherein $R_8$ and $R_9$ are independently H or $C_1$–$C_6$ alkyl, aryl, aralkyl, alkylaryl, or cycloalkyl, and X is a halogen, with the proviso that when n is 0, $R_3$, $R_4$, $R_5$ and $R_6$ can not all be H.

2. The compound of claim 1, wherein $R_1$ is H, substituted or unsubstituted alkyl, —O—CO—$R_7$ or —$CO_2R_7$.

3. The compound of claim 2, wherein $R_1$ is H.

4. The compound of claim 2, wherein $R_1$ is —$CO_2R_7$.

5. The compound of claim 1, wherein G is n-propyl.

6. The compound of claim 1, wherein G is n-butyl.

7. The compound of claim 1, wherein $R_2$ is halogen.

8. The compound of claim 7, wherein $R_2$ is F.

9. The compound of claim 1, wherein n is 1.

10. The compound of claim 1, wherein $R_3$=$R_4$=H and $R_5$ is =O.

11. The compound of claim 1, wherein $R_3$ and $R_4$ are on the same carbon of ring T and are independently —$CH_3$ and —C(O)—NH—aryl, $R_5$=O and $R_6$ is H.

12. The compound of claim 1, wherein $R_3$ is methyl, $R_4$ is an amide and $R_5$=$R_6$=H.

13. The compound of claim 12, wherein said $R_3$ and $R_4$ are on the same carbon of ring T.

14. The compound of claim 1, wherein $R_3$=$CH_2OR_{10}$ and $R_4$=$R_5$=$R_6$=H, where $R_{10}$ is H or $CH_3$.

15. The compound of claim 1, wherein $R_3$ and $R_4$ are on the same carbon of ring T and are independently —OH and 2-pyridyl, and $R_5$=$R_6$=H.

16. The compound of claim 1, wherein said pharmaceutically acceptable salt is a hydrochloride.

17. A compound of the formula:

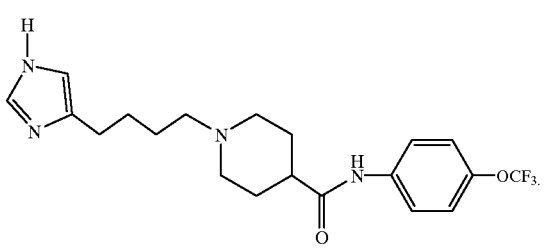

18. A compound of the formula:

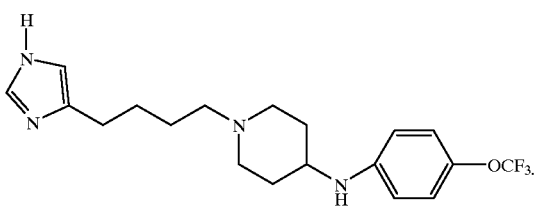

19. A pharmaceutical composition for use in treating allergy, inflammation, hypertension, glaucoma, sleeping disorders, states of hyper-motility of the gastrointestinal tract, Alzheimers, Schizophrenia and migraines, said composition comprising a therapeutically effective amount of a compound of claim 1 and a pharmaceutically acceptable carrier.

20. A method of treating allergy, inflammation, hypertension, glaucoma, sleeping disorders, states of hyper-motility of the gastrointestinal tract, Alzheimers, Schizophrenia and migraines, said method comprising administering a antihistaminically effective amount of a compound of claim 1 to a patient in need of such a treatment.

21. A method of preparing a pharmaceutical composition comprising admixing a compound of claim 1 with a pharmaceutically acceptable carrier.

22. A method of preparing a compound of claim 1, as outlined in the scheme:

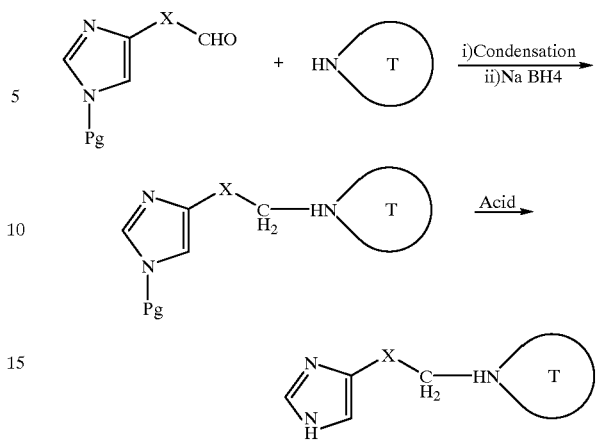

said method comprising: (i) reacting an imidazolylalkyl-substituted aldehyde with an amine of ring T in an organic solvent at a temperature of about $-20°$ C. to about $150°$ C. to form an enamine, and (ii) reducing said enamine to yield an imidazolylalkyl substituted amine (of ring T), wherein $R_1$, $R_2$ and T are as defined in claim 1.

23. The method of claim 22, wherein $R_1$ is H or triphenylmethyl, $R_2$=H and ring T carries a —$CO_2Et$ substituent on position 4 with respect to said amine nitrogen.

24. The method of claim 23, wherein said triphenylmethyl is subsequently hydrolyzed to form $R_1$=H.

25. The method of claim 23, further comprising reacting said —$CO_2Et$ substituent on ring T with an amine to form an amide.

26. The method of claim 25, further comprising reducing said amide to form a second amine substituent on said ring T.

27. The method of claim 26, further comprising reacting said second amine substituent with a sulfonyl halide to form a sulfonamide.

* * * * *